United States Patent
Dresher

(10) Patent No.: US 10,925,512 B2
(45) Date of Patent: Feb. 23, 2021

(54) USE OF LOW-POWER RF ENERGY FOR TISSUE DIAGNOSIS

(71) Applicant: Boston Scientific Scimed, Inc., Maple Grove, MN (US)

(72) Inventor: Russell P. Dresher, Hudson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 842 days.

(21) Appl. No.: 15/454,203

(22) Filed: Mar. 9, 2017

(65) Prior Publication Data

US 2017/0258361 A1 Sep. 14, 2017

Related U.S. Application Data

(60) Provisional application No. 62/306,441, filed on Mar. 10, 2016.

(51) Int. Cl.
| | | |
|---|---|---|
| *A61B 5/07* | (2006.01) | |
| *A61B 5/053* | (2006.01) | |
| *A61B 5/00* | (2006.01) | |
| *A61B 5/0507* | (2021.01) | |

(52) U.S. Cl.
CPC ................ *A61B 5/07* (2013.01); *A61B 5/053* (2013.01); *A61B 5/0507* (2013.01); *A61B 5/6853* (2013.01); *A61B 5/6858* (2013.01)

(58) Field of Classification Search
CPC ......... A61B 5/07; A61B 5/0507; A61B 5/053; A61B 5/6853; A61B 5/6858
USPC .......................................... 600/547
See application file for complete search history.

(56) References Cited

U.S. PATENT DOCUMENTS

| | | | |
|---|---|---|---|
| 4,936,281 A * | 6/1990 | Stasz ..................... | A61B 5/042 600/439 |
| 6,019,757 A * | 2/2000 | Scheldrup ........ | A61B 17/12109 606/49 |
| 7,104,987 B2 * | 9/2006 | Biggs ...................... | A61N 1/06 606/34 |
| 8,002,744 B2 | 8/2011 | Pepper et al. | |
| 8,774,913 B2 | 7/2014 | Demarais et al. | |
| 9,770,293 B2 * | 9/2017 | Dresher ............. | A61B 18/1492 |
| 9,827,039 B2 * | 11/2017 | Dandler ............. | A61B 18/1492 |
| 2003/0236455 A1* | 12/2003 | Swanson ............ | A61B 18/1492 600/374 |
| 2006/0247746 A1* | 11/2006 | Danek ................... | A61B 34/20 607/115 |
| 2009/0030477 A1* | 1/2009 | Jarrard ............... | A61B 18/1206 607/42 |
| 2010/0185192 A1 | 7/2010 | Muller et al. | |
| 2013/0090652 A1* | 4/2013 | Jenson ............... | A61B 18/1492 606/41 |
| 2013/0282000 A1 | 10/2013 | Parsonage | |
| 2013/0324995 A1 | 12/2013 | Dresher | |
| 2014/0128859 A1 | 5/2014 | Lee | |
| 2014/0180196 A1 | 6/2014 | Stone et al. | |

* cited by examiner

*Primary Examiner* — Navin Natnithithadha
(74) *Attorney, Agent, or Firm* — Kacvinsky Daisak Bluni PLLC

(57) ABSTRACT

The embodiments described herein relate to devices, systems and methods for in-vivo diagnosis of disease-state tissue within a body.

20 Claims, 4 Drawing Sheets

USE OF LOW-POWER RF ENERGY FOR TISSUE DIAGNOSIS

STATEMENT OF RELATED APPLICATION

This application claims the benefit of U.S. Provisional Application Ser. No. 62/306,441, filed Mar. 10, 2016 and entitled "USE OF LOW-POWER RF ENERGY FOR TISSUE DIAGNOSIS", which is hereby incorporated by reference.

FIELD OF THE DISCLOSURE

Embodiments described herein relate to devices, systems and methods for in-vivo diagnosis of disease-state tissue within a body, for example, within a passageway within a body. In particular, embodiments of the present disclosure relate to devices, systems and methods for diagnosing tissue by delivering low power radiofrequency energy to tissue within a body and monitoring, for example, a reflected portion of the energy delivered to the tissue during the tissue diagnosis procedure.

BACKGROUND OF THE DISCLOSURE

There are currently many methods of detecting disease-state tissue in-vivo. Various methods rely on some sort of imaging principle to identify suspect areas for subsequent biopsy or treatment. Current methods have varying degrees of success rate and complexity. A compounding factor in disease state tissue detection, particularly in small passageways, is that the tissue is often difficult to visualize in high-definition because the imaging system is often too small to support high definition cameras. Furthermore, disease state tissue can lie below the surface (e.g., the submucosa) making direct visualization impossible.

SUMMARY

Embodiments of the present disclosure include those directed to devices, systems and methods for diagnosing disease-state tissue within a body, for example, within a passageway within a body.

In various aspects, the present disclosure pertains to a method for diagnosing tissue in a body, for example, within a passageway within a body. The method comprises: (a) positioning a medical device adjacent a diagnosis site adjacent the tissue, the medical device comprising (i) an elongate member having a proximal end and a distal end and (ii) an energy emitting portion comprising at least one electrode adjacent the distal end; (b) supplying an amount of low-power RF energy from an energy source to the energy emitting portion to diagnose tissue at the diagnosis site, a first portion of the amount of low-power RF energy being transmitted through the energy emitting portion to the tissue and a second portion of the amount of low-power RF energy being reflected back towards the proximal end of the elongate member (with the first portion and second portion each representing a percentage of the amount of low-power RF energy that is supplied); and (c) monitoring a signal corresponding to the second portion.

In certain embodiments, which can be used in conjunction with any of the above aspects, the power of the second portion, the voltage of the second portion, or both the power and voltage of the second portion may be measured.

In certain embodiments, which can be used in conjunction with any of the above aspects and embodiments, the method further comprises monitoring a signal corresponding to the first portion.

In certain embodiments, which can be used in conjunction with any of the above aspects and embodiments, the method further comprises expanding the energy emitting portion from a collapsed configuration to an expanded configuration such that the at least one electrode contacts tissue.

In certain embodiments, which can be used in conjunction with any of the above aspects and embodiments, the method further comprises advancing the energy emitting portion along a passageway in the body. In such embodiments, the signal may be, for example, monitored continuously as the energy emitting portion is advanced along the passageway or monitored at a plurality of discrete positions along the passageway.

In certain embodiments, which can be used in conjunction with any of the above aspects and embodiments, the signal may be monitored for each of a plurality of electrodes. In certain such embodiments, the monitored signal may be, for example, compared to a threshold value, compared to a signal monitored for another electrode, and/or compared to a baseline signal based on a collection of electrodes.

In certain embodiments, which can be used in conjunction with any of the above aspects and embodiments, the low-power RF energy may have an energy level that is sufficiently high for diagnosis, while being sufficiently low to avoid tissue damage.

In certain embodiments, which can be used in conjunction with any of the above aspects and embodiments, the low-power RF energy may have an energy level ranging from 0.1 dBm or less to 20 dBm or more, for example, ranging from 0.1 to 0.2 to 0.5 to 1 to 2 to 5 to 10 to 20 dBm (i.e., ranging between any two of the preceding values).

In various aspects, the present disclosure pertains to a system for diagnosing tissue within a body, for example, tissue of a passageway within a body. The system may comprise: (a) an energy source; (b) a medical device configured to deliver energy to a diagnosis site adjacent the tissue, the medical device comprising (i) an elongate member having a proximal end and a distal end and (ii) an energy emitting portion comprising at least one electrode adjacent the distal end of the elongate member, the medical device being configured to receive an amount of low-power RF energy from the energy source and to transmit a first portion of the amount of low-power RF energy through the energy emitting portion to adjacent tissue; (c) one or more components configured to detect at least a signal corresponding to a second portion of the amount of low-power RF energy that is reflected back towards the proximal end of the elongate member; and (d) a controller configured to analyze the signal to determine the state of diagnosis.

In certain embodiments, the one or more components may comprise a bi-directional coupler that is configured to detect a signal corresponding to the first portion of the amount of low-power RF energy and the signal corresponding to the second portion of the amount of low-power RF energy.

In certain embodiments, which can be used in conjunction with any of the above aspects and embodiments, the energy source may comprise a low-power RF generator.

In certain embodiments, which can be used in conjunction with any of the above aspects and embodiments, the energy emitting portion may comprise a plurality of electrodes.

In certain embodiments, which can be used in conjunction with any of the above aspects and embodiments, the energy emitting portion may comprise an expandable member upon which the electrodes are positioned.

In certain embodiments, which can be used in conjunction with any of the above aspects and embodiments, the expandable member may comprises an expandable frame and/or an expandable balloon upon which the electrodes are positioned. The electrodes may be positioned, for example, around a circumference of the expandable member, for instance, equally spaced around a circumference of the expandable member.

In certain embodiments, which can be used in conjunction with any of the above aspects and embodiments, the electrodes may be elongated electrodes that extend lengthwise along the expandable member. For example the elongated electrodes may have a (length-to-width) aspect ratio ranging from 2:1 to 5:1 to 10:1 to 20:1 or more.

DETAILED DESCRIPTION

Figure 1:
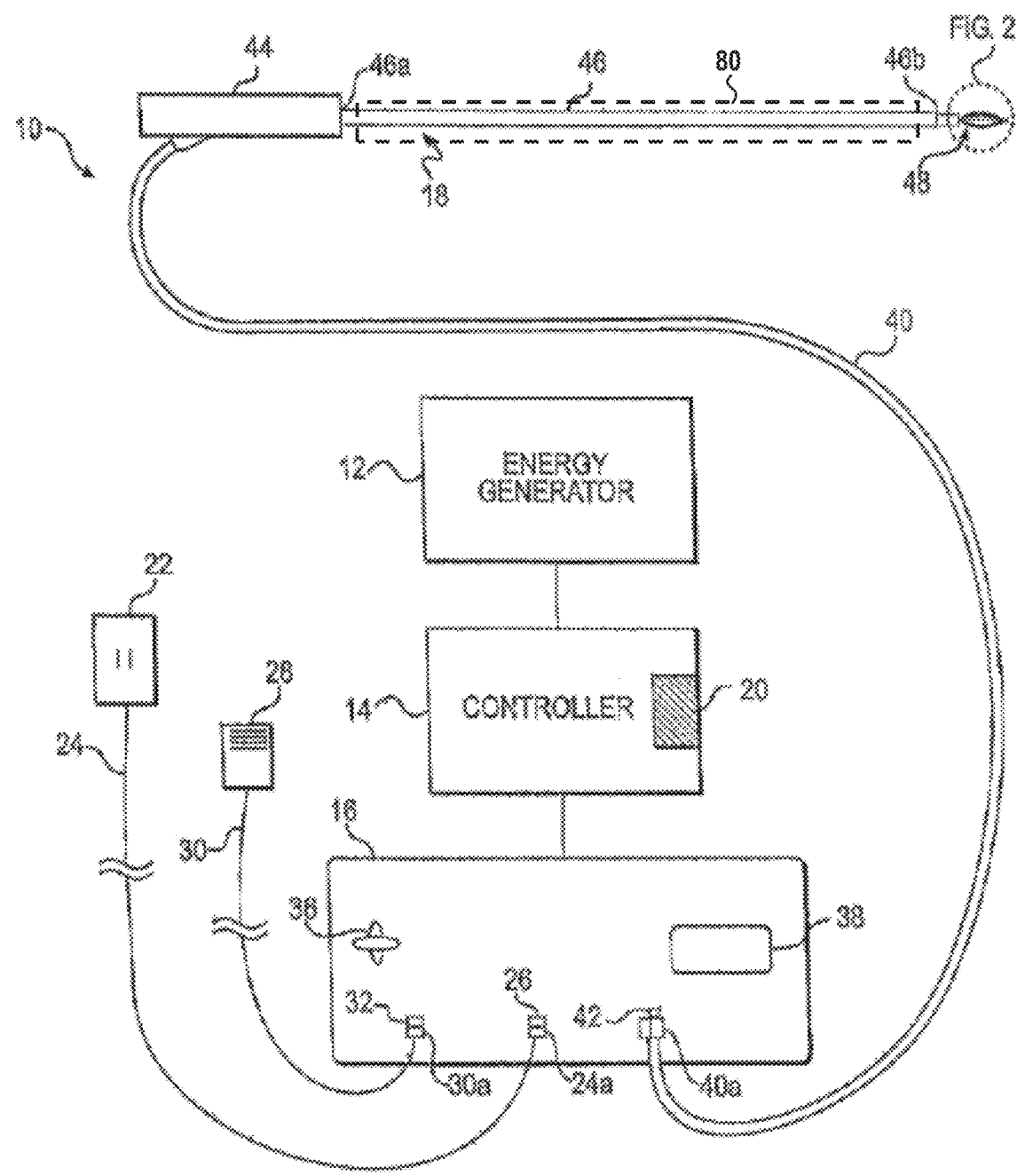
FIG. 1 is a schematic illustration of a system for diagnosing tissue in a passageway within a body, the system including a low power radiofrequency energy delivery device having an energy emitting portion, according to an embodiment of the present disclosure.

Reference will now be made in detail to exemplary embodiments of the present disclosure, examples of which are illustrated in the accompanying drawings. Whenever possible, the same reference numbers will be used throughout the drawings to refer to same or like parts.

Generally described, the present disclosure relates to devices, systems and methods for diagnosing tissue by delivering low-power radiofrequency (RF) energy to tissue with a body, more typically, to tissue within the wall of a passageway in a patient's body and monitoring reflected power or voltage. "Passageway" as used herein refers to and includes any lumen, duct, cavity, space, or like within the body. Exemplary passageways include the esophagus, colon, common bile duct, pancreatic duct and blood vessels, among others. In this regard, the present disclosure is directed to the detection of disease-state tissue, for example, cancer tissue, through a low-power RF technique for in-vivo diagnosis in which changes in tissue impedance are detected by measuring changes in reflected power of a low-power RF signal during a scan.

In certain embodiments, the low-power RF energy may have a low-power energy level that is sufficiently high for diagnosis, while being sufficiently low to avoid tissue damage.

In certain embodiments, the low-power RF energy may have a low-power energy level ranging from 0.1 dBm or less to 20 dBm or more, for example, ranging from 0.1 to 0.2 to 0.5 to 1 to 2 to 5 to 10 to 20 dBm (i.e., ranging between any two of the preceding values).

In this regard, impedance refers to an opposition to the flow of electrical current through the tissue. Reflected power is a function of the impedance mismatch between an RF signal generator (e.g., a controller) and a load (e.g., tissue).

Radio frequency (RF) as defined herein is any of the electromagnetic wave frequencies that lie in the range of 3 kHz-300 GHz. RF energy delivered in accordance with the present disclosure may be selected from any portion of this range, for example, ranging from 3 kHz to 10 kHz to 30 kHz to 100 kHz to 300 kHz to 1 MHz to 3 MHz to 10 MHz to 30 MHz to 100 MHz to 300 MHz to 1 GHz to 3 GHz to 10 GHz to 30 GHz to 100 GHz to 300 GHz (i.e., ranging between any two of the preceding values). In certain embodiments, the range selected may optimized based on a tissue penetration depth of less than 1 cm. In certain embodiments, the frequency range of 1 MHz to 300 MHz may be less desirable due to potential ablation effects.

The power delivered to a load by an RF signal, $P_{load}$, often expressed in units of dB (decibels) or dBm (decibel milliwatts), is defined as:

$$P_{load} = \left[\frac{|V_f|^2}{Z_0} - \frac{|V_r|^2}{Z_0}\right],$$

where $V_f$ is forward voltage, $V_r$ is the reflected voltage, and $Z_0$ is the transmission line impedance. In general, power with respect to voltage is defined as:

$$P = \frac{|V|^2}{Z_0}.$$

Therefore, the power delivered to a load is a function of both forward and reflected power. As reflected power increases, the power delivered to load decreases. Reflected voltage (and reflected power) increase due to impedance mismatches between the RF signal generator and load as defined by:

$$V_r = \frac{V - (Z_0 \cdot I)}{2},$$

where V is source voltage and I is source current. For $V=Z_0 I$, $V_r=P_r=0$ and therefore the power delivered to the load will be equal to $P_f$, where $P_f$ is forward power.

Biological tissue possesses a characteristic impedance depending upon its molecular composition. For instance, it is understood that cancerous tissue generally possesses a lower characteristic impedance compared to that of healthy tissue of the same type. Other disease states are also expected to have impedance differences compared to healthy tissue.

Consequently, a controller may be tuned such that the transmission line impedance is similar to that of healthy tissue associated with the diagnosis site, resulting in small amounts of reflected power. In this regard, the impedance of the transmission line, which includes the signal path from generator to the probe, should be well understood and in some embodiments, may be tuned to the match the load anticipated for healthy tissue. A transmission line tuned to have impedance equal to the tissue load will result in minimal (theoretically zero) reflected power. During diagnosis, tissue impedance changes will result in differences in reflected power, increasing impedance mismatch resulting in an increase in reflected power. A reflected power threshold may be identified to indicate a disease state. Methods based on is principle may allow for detection below the visible surface, and for mucosa-lined passageways, may improve detection within the submucosa.

In the present disclosure an RF probe including one or more electrodes and an RF controller including an RF generator, may be used as a diagnostic system. The RF probe may be re-usable or disposable. In certain embodiments, the system may further include a catheter (i.e., a tube, including vascular catheters, endoscopes, etc.), which may be re-usable or disposable, and which may be provided in various sizes depending on the anatomy intended to be analyzed. The catheter may be provided with visualization to guide the physician and may be provided with a working channel through which the RF probe may be passed.

In this regard, the RF probe may be passed through the catheter to the distal tip. A health care professional can then pass the probe over the anatomy. For improved accuracy, the probe preferably stays in contact with tissue while at the same time being atraumatic. The RF controller may be configured to deliver low-power RF energy, typically an energy level that is sufficiently high for diagnosis, while being sufficiently low to avoid tissue damage (e.g., maintaining cells of tissue being diagnosed to 40° C. or less), to the probe. The RF controller may also be configured to control the electrode state, delivering RF energy to the active electrode(s) at the tissue interface and measuring reflected power from the tissue. Algorithms may be used to control the electrode state with respect to time.

Turning now to the drawings, FIG. 1 illustrates an exemplary system 10. System 10 includes an energy generator 12, a controller 14, a user interface 16, and a probe 18. Energy generator 12 may be any suitable device configured to produce low-power RF energy for diagnosing tissue as described herein. The RF energy generator may be configured to emit energy at specific frequencies and for specific amounts of time.

More particularly, energy generator 12 may be configured to generate energy with a wattage output sufficient to diagnose tissue without harming (ablating) the tissue.

An energy controlling mechanism 22 may be associated with energy generator 12. Energy controlling mechanism 22 may be any suitable automatic and/or user operated device in operative communication with energy generator 12 via a wired or wireless connection, such that energy controlling mechanism 22 may be configured to enable activation of energy generator 12. Energy controlling mechanism 22 may therefore include a switch, a push-button, or a computer, among other possibilities. In the exemplary embodiment of FIG. 1, energy controlling mechanism 22 is a footswitch. A conductive cable 24 may extend from energy controlling mechanism 22 to user interface 16, and may include a coupler 24a configured to be electrically coupled to an interface coupler 26 disposed on user interface surface 16.

Controller 14 may be coupled to energy generator 12. Controller 14 may include a processor 20 configured to produce signals for controlling the energy generator 12, receive information feedback signals (e.g., reflected signals), process the information feedback signals according to various algorithms, and produce signals directed to visual and/or audio indicators. For example, processor 20 may include one or more integrated circuits, microchips, microcontrollers, and/or microprocessors, which may be all or part of a central processing unit (CPU), a digital signal processor (DSP), an analog processor, a field programmable gate array (FPGA), or any other circuit known to those skilled in the art that may be suitable for executing instructions or performing logic operations. That is, processor 20 may include any electric circuit that may be configured to perform a logic operation on at least one input variable. In some embodiments, processor 20 may be configured to use a control algorithm to analyze a reflected portion and/or a forward portion of the energy delivered to targeted tissue and generate control signals for energy generator 12.

Controller 14 may additionally be coupled to and in communication with user interface 16. In the exemplary embodiment illustrated in FIG. 1, controller 14 may be electrically coupled to user interface 16 via a wire connection. In alternative embodiments, controller 14 may be in wireless communication with user interface 16. User interface 16 may be any suitable device capable of providing information to an operator of the energy delivery system 10. Accordingly, user interface 16 may be configured to be operatively coupled to each of the components of energy delivery system 10, receive information signals from the components, and output at least one visual or audio signal to a device operator in response to the information received. In the exemplary embodiment, the surface of user interface 16 includes at least one switch 36 and a display 38. It is contemplated that user interface 16 may additionally include one or more audio tone indicators and/or graphical representations of components of system 10.

Probe 18 may be coupled to user interface 16. For example, a cable 40 may extend from probe 18 to user interface 16, and include a coupler 40a configured to be electrically coupled to an interface coupler 42 associated with user interface 16.

Probe 18 may include a handle portion 44, an elongate member 46, and an energy emitting portion 48. In certain embodiments, one or more of the user interface 16, controller 14 and energy generator 12 may be integrated into the handle portion 44. Elongate member 46 has a proximal end 46a and a distal end 46b. As used herein, "proximal" refers to the end closer to the device operator during use, and "distal" refers to the end further from the device operator during use. Thus, handle portion 44 may be disposed at proximal end 46a of elongate member 46 and energy emitting portion 48 may be disposed at distal end 46b. Handle portion 44 may be any suitable handle and may have one or more actuators, switches, or the like to control movement of elongate member 46 and/or manipulate energy emitting portion 48.

Elongate member 46 extends distally from handle portion 44. Elongate member 46 may be a flexible tube, made from any suitable biocompatible material having sufficient flexibility to traverse non-linear anatomy. Such materials may include, but are not limited to, rubber, silicon, other polymers, metal-polymer composites, metals including metal alloys of one or more of nickel, titanium, copper cobalt, vanadium, chromium or iron (e.g., stainless steel), superelastic material such as nitinol, which is a nickel-titanium alloy.

Elongate member 46 and energy emitting portion 48 may be provided with a coating. The coating may be any coating known to those skilled in the art enabling ease of movement of probe 18 through an access device such as a catheter and/or a passageway within a patient's body. The coating may include a lubricious coating and/or an anesthetic.

As indicated above, in some embodiments, system may further include a catheter 80 (represented by dashed lines) that includes an elongate member with one or more lumens or channels formed therein for the passage of a variety of surgical equipment, including, but not limited to, probe 18, imaging devices and tools for irrigation, insufflation, vacuum suctioning, biopsies, and drug delivery. The catheter may include an imaging device mounted at the distal end of the catheter. The catheter may include an atraumatic exterior surface having a rounded shape and/or a coating like that described above.

Energy emitting portion 48 may be attached to and extend from distal end 46b of elongate member 46. Energy emitting portion 48 may be formed from the same piece of material as elongate member 46. Alternatively, energy emitting portion 48 may be fabricated independently of elongate member 46 by any known means and may be made permanently or removably attached to distal end 46b of elongate member 46. For example, energy emitting portion 48 may be permanently or removably attached to distal end 46b of elongate member 46 via a flexible junction enabling movement of energy emitting portion 48 relative to distal end 46b of elongate member 46.

Figure 2:
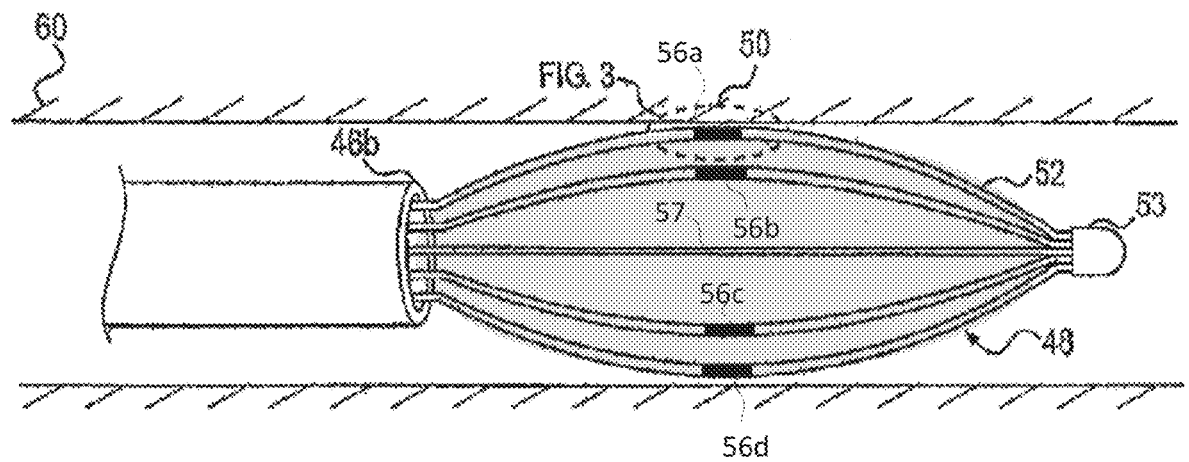
FIG. 2 is a schematic side view of the energy emitting portion of FIG. 1, according to an embodiment of the present disclosure.

Referring to FIG. 2, energy emitting portion 48 may be any size, shape and/or configuration having dimensions that can be inserted into a passageway within a body and advanced to a diagnosis site 60. In the embodiment shown, energy emitting portion 48 may comprise an expandable frame that is configured to be advanced to the diagnosis site in a first, collapsed configuration (not shown) whereupon it takes on a second, expanded configuration as shown once positioned at a diagnosis site 60 in a passageway. For example, the expandable frame may be advanced to the diagnosis site 60 within a catheter at which point the expandable frame is advanced relative to the catheter and/or the catheter is retracted relative to the expandable frame, such that the expandable frame extends beyond a distal end of the catheter. In some embodiments, the frame has a shape memory and is maintained in a first, collapsed position by walls of the catheter and subsequently expands to a second, expanded configuration at the diagnosis site 60 when freed from the catheter as a result of the shape memory. In other embodiments, one or more actuators, which may be operated from the handle portion 48, may be used to lengthen the frame during advancement in a first, collapsed configuration, after which the frame may subsequently be expanded into a second, expanded configuration at the diagnosis site 60, for example, by providing the frame with a shape memory effect that causes the frame to radially expand or by using the actuator to shorten length of the frame, thereby causing the frame to radially expand. In still other embodiments, the energy emitting portion 48 may comprise an expandable balloon is configured to be advanced to the diagnosis site 60 in a first, collapsed state and take on a second, expanded configuration by inflating the balloon once positioned at a diagnosis site 60 in a passageway. Once in a second, expanded configuration, a contact region 50 of energy emitting portion 48 may be configured to contact tissue at diagnosis site 60.

Energy emitting portion 48 may have any shape, size, and/or configuration in the second, expanded configuration. In the exemplary embodiment shown in FIG. 2, energy emitting portion 48 comprises a having a plurality of curved legs 52 that converge at a distal tip 53. Also shown is an actuation rod 57 for lengthening and shortening the frame. Legs 52 may be configured so that the legs 52 correspond to lines drawn along a surface of an imaginary prolate spheroid (represented by shaded area) in the second, expanded configuration. In this embodiment, region 50 may be the portion of frame that is the greatest distance from the longitudinal axis of energy emitting portion 48 when energy emitting portion 48 is in the second, expanded configuration. It is contemplated that legs 52 may form any other shape and/or configuration that facilitates contact between contact region 50 and tissue of diagnosis site 60 in the second, expanded configuration.

Legs 52 may be constructed from a material such as, for example, a shape memory metal or metal alloy or a polymeric material so that legs 52 may collapse to have a smaller cross-section in the first, collapsed configuration (not shown). Although FIG. 2, shows that that energy emitting portion 48 comprises four legs 52, energy emitting portion 48 may include any number of legs 52 (e.g., 2, 3, 5, 6, 7, 8, etc. legs) having any desired pattern and/or configuration. For example, legs 52 may correspond to a surface of an imaginary cylinder or any other suitable shape. In addition, legs 52 may have any cross-sectional shape including, but not limited to, circular, square, or ovular.

Figure 3:
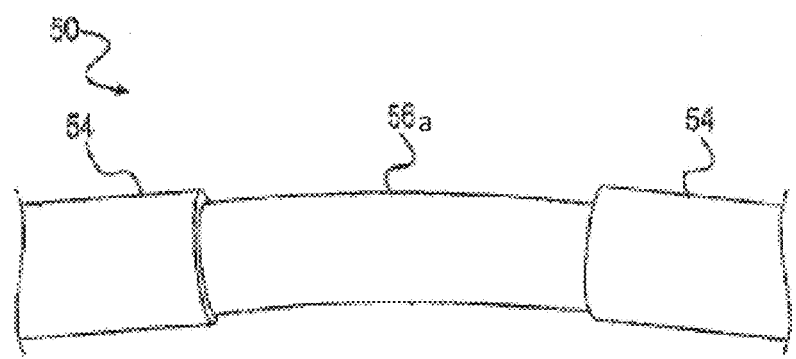
FIG. 3 is an exploded view of a portion of a leg of the energy emitting portion of FIG. 2, according to an embodiment of the present disclosure.

Energy emitting portion 48 may further include at least one electrode 56. The at least one electrode 56 may be located along the length of at least one of the plurality of legs 52 and may include at least a portion of the contact region 50 of energy emitting portion 48. In the exemplary embodiment illustrated in FIG. 3, the at least one leg 52 of the energy emitting portion 48 comprises a single, elongate conducting element, portions of which may be covered by an insulating material 54, such as, for example, a non-conducting polymeric sheath that is heat shrunk onto each leg 52. In addition, another portion of the elongate conducting element disposed between the insulated portions 54 is exposed, forming an electrode 56 for delivering energy to tissue at diagnosis site 60. The electrode 56 may be, for example, any suitable electrode known to those skilled in the art configured to emit RF energy. In the embodiment of FIG. 2, four electrodes 56a, 56b, 56c, 56d are shown. The electrodes 56a, 56b, 56c, 56d may be operated in monopolar mode or bipolar mode.

In embodiments where energy emitting portion 48 includes monopolar electrodes 56a, 56b, 56c, 56d, system 10 further includes a return electrode component configured to complete an electrical energy emission or patient circuit between energy generator 12 and a patient (not shown). Referring to FIG. 1, the return electrode component may include a conductive pad 28 for this purpose. Conductive pad 28 may include a conductive adhesive surface configured to removably adhere to a patient's skin. In addition, conductive pad 28 may include a surface area having a sufficient size in order to alleviate burning or other injury to the patient's skin that may occur in the vicinity of the conductive pad 28 during energy emission. A cable 30 may extend from conductive pad 28 and may include a coupler 30a. Coupler 30a may be configured to be coupled to an interface coupler 32 on a surface of user interface 16 to electrically couple conductive pad 28 to the user interface 16.

In other embodiments, electrodes 56a, 56b, 56c, 56d may be operated in bipolar mode, in which case a separate return electrode component (e.g., conductive pad) is not required, but which may nonetheless be provided in the event that it is also desired to operate the electrodes 56a, 56b, 56c, 56d in monopolar mode. With regard to bipolar mode, for example, electrode 56a may be operated as an active electrode while electrode 56b is simultaneously operated as a return electrode, after which electrode 56a may be operated as a return electrode while electrode 56b is simultaneously operated as an active electrode. Similarly, electrode 56c may be operated as an active electrode while electrode 56d is simultaneously operated as a return electrode, after which electrode 56c may be operated as a return electrode while electrode 56d is simultaneously operated as an active electrode. In other words, electrodes 56a, 56b are operated as a first bipolar pair and electrodes 56c, 56d are subsequently operated as a second bipolar pair.

As another example, electrodes 56a and 56c may be operated as active electrodes while electrodes 56b and 56d, respectively, are simultaneously operated as return electrodes for electrodes 56a and 56c, respectively, after which electrodes 56a and 56c may be operated as return electrodes while electrodes 56b and 56d, respectively, are simultaneously operated as active electrodes. In other words, electrodes 56a, 56b and electrodes 56c, 56d are simultaneously operated as first and second bipolar pairs.

More broadly, the electrodes may be operated as the following bipolar pairs: electrodes 56a, 56b, electrodes 56a, 56c, electrodes 56a, 56d, electrodes 56b, 56c, electrodes 56b, 56d, and electrodes 56c, 56d.

Figure 4:
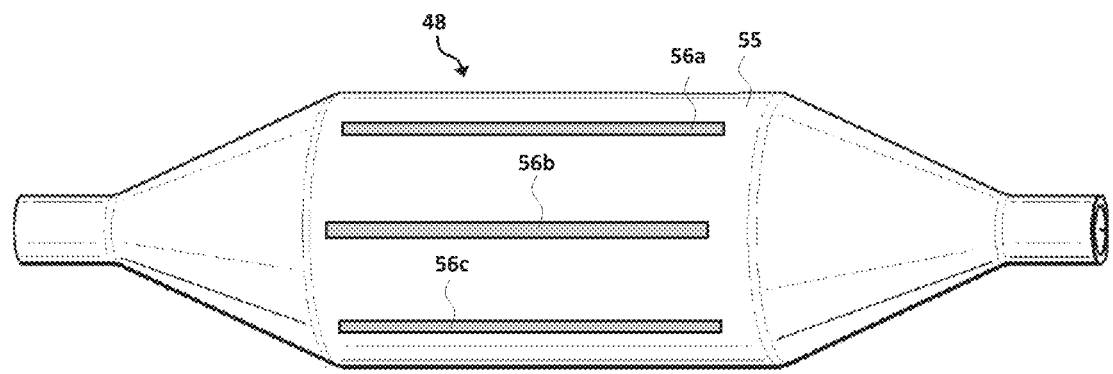
FIG. 4 is a schematic perspective view of an energy emitting portion, according to another embodiment of the present disclosure.

In FIG. 2, the electrodes are placed on an expandable frame that comprises a plurality of legs 12 as structural support members for the electrodes. In another embodiment shown in FIG. 4, an energy emitting portion 48 is shown in which the expandable electrodes placed on a surface of an expandable balloon 55. In the example shown, three electrodes, 56a, 56b, 56c (out of six total electrodes) are shown, which extend longitudinally along a length of the balloon, although energy emitting portion 48 may include any number of electrodes (e.g., 2, 3, 4, 5, 7, 8, etc.) having any desired pattern disposed on the balloon. As in FIG. 2, the electrodes may be operated in monopolar mode or bipolar mode. For example, a balloon formed from a material such as polyimide or polyethylene terephthalate may be patterned with gold electrodes, for example, using processes like those described in U.S. Patent Pub. No. 2014/0128859. Because the electrodes are disposed around the balloon, a scan may be made around a circumference of the energy emitting portion 48, and the balloon need not be rotated inside the lumen.

Figure 5:
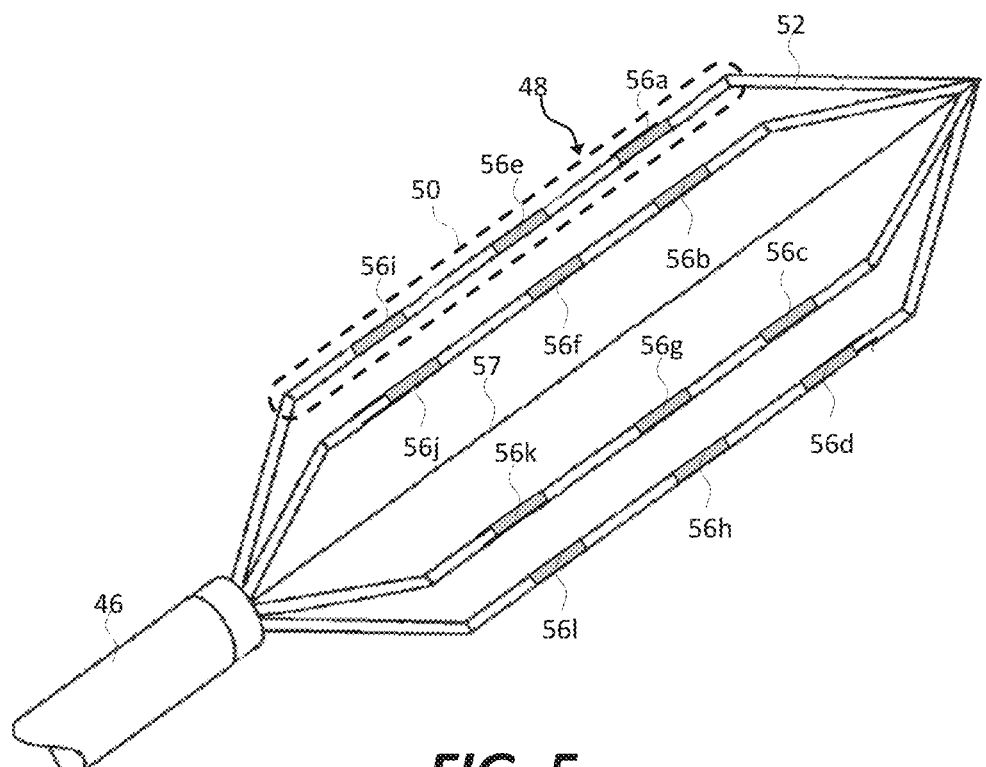
FIG. 5 is a schematic perspective view of an energy emitting portion, according to yet another embodiment of the present disclosure.

While the energy emitting portion 48 of FIG. 2 includes one electrode 56 per leg. In other embodiments, a plurality of electrodes is provided along a length of each leg. With reference now to FIG. 5, an energy emitting portion 48 is shown in which three electrodes are located along the length of at least one of the plurality of legs 52 (an analogous distribution of electrodes could be created on a balloon surface). Due to the fact that the outermost radial portions of the legs 12 linear, the contact region 50 of the energy emitting portion 48 is significantly longer than that of FIG. 2. Twelve electrodes 56a, 56b, 56c, 56d, 56e, 56f, 56g, 56h, 56i, 56j, 56k, 56l are shown. As in FIG. 2, the electrodes 56a, 56b, 56c, 56d, 56e, 56f, 56g, 56h, 56i, 56j, 56k, 56l may be operated in monopolar mode or bipolar mode.

In one specific example, among other possibilities, the following electrodes may be operated as bipolar pairs at a given longitudinal position on the energy emitting portion 48: (a) adjacent electrodes 56a, 56b, electrodes 56b, 56c, electrodes 56c, 56d and electrodes 56d, 56a, as well as non-adjacent electrodes 56a, 56c and electrodes 56b, 56d, (b) adjacent electrodes 56e, 56f, electrodes 56f, 56g, electrodes 56g, 56h and electrodes 56h, 56e, as well as non-adjacent electrodes 56e, 56g and electrodes 56f, 56h, (c) adjacent electrodes 56l, 56j, electrodes 56j, 56k, electrodes 56k, 56l and electrodes 56l, 56i, as well as non-adjacent electrodes 56i, 56k and electrodes 56j, 56l. In this way, a scan may be made around a circumference of the energy emitting portion 48 at three different longitudinal positions along the energy emitting portion 48 without moving the energy emitting portion 48.

In another specific example, among other possibilities, the following electrodes may be operated as bipolar pairs at a given angular position on the energy emitting portion 48 (i.e., a given angle of rotation around the longitudinal axis of the on the energy emitting portion 48): (a) electrodes 56i, 56e, electrodes 56e, 56a, electrodes 56i, 56a, (b) electrodes 56j, 56f, electrodes 56f, 56b, electrodes 56j, 56b, (c) electrodes 56k, 56g, electrodes 56g, 56c, electrodes 56k, 56c, (d) electrodes 56l, 56h, electrodes 56h, 56d, electrodes 56l, 56d. In this way, a length of tissue along the diagnosis site can be scanned without moving the energy emitting portion 48. In this way, a scan may be made along the length of the energy emitting portion 48 at four different angles of rotation around the axis of the energy emitting portion 48 without moving the energy emitting portion 48.

Figure 6:
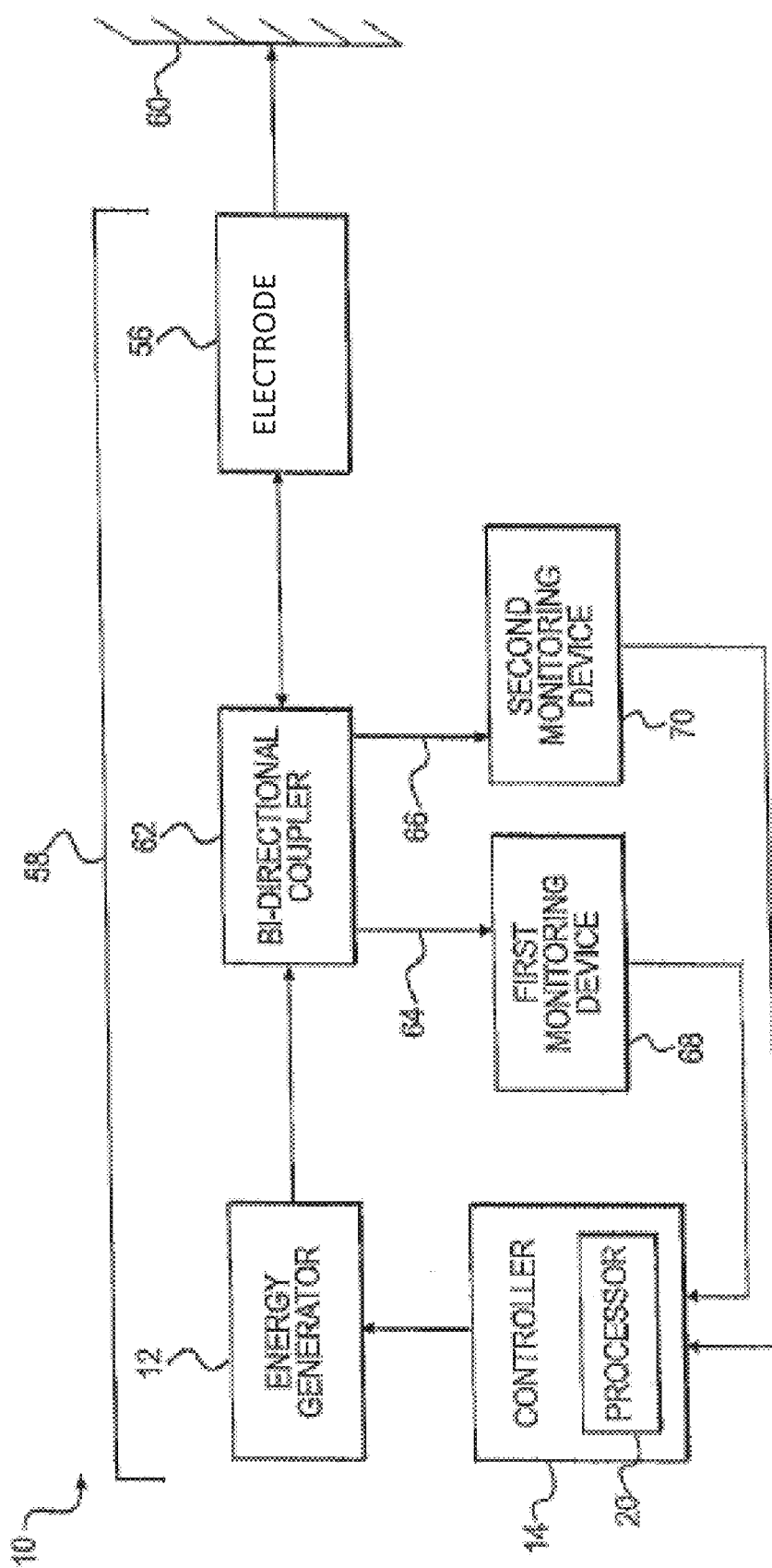
FIG. 6 is a schematic diagram of the system of FIG. 1, according to an embodiment of the disclosure.

FIG. 6 is a simplified representation of system 10. As will be described below, components of system 10 may be configured to deliver energy to tissue at diagnosis site 60 and to monitor a reflected portion of that energy.

With reference to FIG. 6, energy generator 12 of system 10 may be controlled by controller 14, and may be configured to generate a forward signal for delivering energy to tissue at diagnosis site 60. As discussed above, energy generator 12 may be an RF generator configured to generate a forward RF signal. The forward RF signal may be carried to the at least one electrode 56 in contact with tissue at diagnosis site 60 via transmission line 58. Transmission line 58 broadly refers to any structure or structures designed to carry alternating current of, for example, radio frequency. In the exemplary embodiment, transmission line 58 may include energy generator 12, the at least one electrode 56, and conducting elements therebetween including, but not limited to, cable 40, and conductors within the elongate member 46 and energy emitting portion 48.

The forward RF signal carried via transmission line 58 may be supplied to the at least one electrode 56. The at least one electrode 56 may then deliver energy to tissue at diagnosis site 60. In particular, low-power RF energy may be delivered through the electrode 56 in contact with tissue at diagnosis site 60 in order to analyze tissue at the diagnosis site.

As will be described in more detail below, system 10 may be configured to analyze tissue at the diagnosis site 60 using a reflected portion of the energy delivered to the at least one electrode 56. The reflection of energy may be a function of the impedance of tissue at diagnosis site 60.

As indicated above, when the impedance of transmission line 58 is tuned to match the impedance of the load (in this case comprising the impedance of the tissue at diagnosis site 60), a substantial portion of the energy delivered via transmission line 58 may be transmitted through the at least one electrode 56 to tissue at diagnosis site 60. When the impedance of the transmission line 58 and the impedance of the tissue at diagnosis site 60 are not matched, a portion of energy supplied to electrode 56 may be reflected back along transmission line 58 to energy generator 12 via secondary signals. The secondary signals may have reflected power. As indicated above, having the ability to measure reflected power provides the possibility to monitor tissue impedance.

The magnitude of the reflected power may be proportional to the mismatch between the impedance of transmission line 58 and the impedance of tissue at diagnosis site 60. That is, the magnitude of the reflected power may increase as the impedance of tissue at diagnosis site 60 decreases from a matched impedance value during diagnosis. In addition, the net forward power, which is approximately equal to the difference between the forward power (associated with the forward signal) and the reflected power (associated with the secondary signal), may decrease.

The system 10 may be provided with ability to measure both forward and reflected power, with suitable methods and devices for doing so determined by one of ordinary skill in the art. As illustrated in FIG. 6, system 10 may include a bi-directional coupler 62 for detecting the reflected power and the forward power of the primary RF signal carried via transmission line 58. Bi-directional coupler 62 may be positioned between energy generator 12 and the at least one electrode 56, and in communication with energy generator 12 and the at least one electrode 56. In some embodiments, bi-directional coupler 62 may be integrally provided with energy generator 12. In other embodiments, bi-directional coupler 62 may be a separate component placed between energy generator 12 and the at least one electrode 56. As shown in FIG. 6, the primary RF signal may be inputted to bi-directional coupler 62. The primary RF signal may pass therethrough unaffected and may be outputted from bi-directional coupler 62 to be transmitted to the at least one electrode 56.

Bi-directional coupler 62 may be any known coupler configured to provide one or more signal sample outputs for measurement. In the exemplary embodiment, bi-directional coupler 62 may be configured to sample the forward and reflected RF signal passing therethrough and detect the forward power and the reflected power. Bi-directional coupler 62 may output a first signal 64 indicative of the forward power and a second signal 66 indicative of the reflected power to first monitoring device 68 and second monitoring device 70, respectively.

First monitoring device 68 and second monitoring device 70 may be any known electrical component configured to measure a power signal. In some embodiments, one or both of first monitoring device 68 and second monitoring device 70 may be a power meter. First monitoring device 68 and second monitoring device 70 may be in communication with processor 20 either wirelessly or via a wired connection to transmit information relating to the forward power and the reflected power. In this manner, the forward and reflected powers may be measured in real time, and changes in the net power level may be detected. Alternative known means for detecting and measuring the forward power and the reflective power are also contemplated.

Prior to initiating the diagnosis procedure, controller 14 may be configured to tune transmission line 58 to have an impedance that is based on that of healthy tissue at diagnosis site 60. For example, the transmission line 58 may be tuned to have an impedance that is substantially equal to the impedance of the healthy tissue at diagnosis site 60, which will result in a negligible amount of reflected power. The impedance of the healthy tissue may be well-known or may be calculated by any known means such as empirical data and/or clinical measurements.

As diagnosis is initiated, probe 18 may be inserted into and advanced through a passageway within a patient's body to diagnosis site 60. After energy emitting portion 48 has been positioned at diagnosis site 60, energy emitting portion 48 may be expanded from a first, collapsed configuration to a second, expanded configuration so that contact region 50 is placed in contact with tissue at diagnosis site 60.

Energy generator 12 may be continuously activated, or an operator may engage energy controlling mechanism 22 to activate energy generator 12. Activation of energy generator 12 may generate a forward signal, for example, a forward RF signal, for delivery through the least one electrode 56 of energy emitting portion 48 to tissue at diagnosis site. In particular, energy generator 12 may generate a forward signal that may be supplied to the at least one electrode 56 via transmission line 58. The low-power RF energy supplied to the at least one electrode 56 may be delivered to tissue at diagnosis site 60. Accordingly, a portion of the energy supplied to electrode 56 may be reflected back along transmission line 58 to energy generator 12 via secondary signals. The secondary signals have reflected power.

In various embodiments, the energy emitting portion 48 may then be moved longitudinally within the passageway and the reflected power measured continuously during movement or at a plurality of discrete positions along the passageway. As movement progresses, the magnitude of the reflected power may change (i.e., increase or decrease), indicating a change in tissue impedance and thus a change in tissue state. Where the transmission line impedance is matched to that of healthy tissue, an increase in reflected power may indicated the presence of diseased (e.g., cancerous) tissue.

Over the course of the diagnosis, bi-directional coupler 62 may be configured to sample the signal passing therethrough and output a first signal 64 indicative of forward power and a second signal 66 indicative of reflective power to first monitoring device 68 and second monitoring device 70, respectively. In some cases, first signal 64 and second signal 66 may be proportional to the forward power and the reflected power of the forward signal, respectively.

In the exemplary embodiment, second monitoring device 70 may continuously monitor the second signal 66 corresponding to the reflected power. In particular, second monitoring device 70 may monitor second signal 66 to measure the magnitude of the reflective power. Second monitoring device 70 may then transmit the measured value to processor 20.

Where the energy emitting portion 48 contains a plurality of electrodes, each electrode at a different angle of rotation around a longitudinal axis of the energy emitting portion 48 (see, e.g., FIGS. 2 and 4), the reflected power may be analyzed from each electrode, either through operation in unipolar mode or bipolar mode, as each electrode is advanced through the body passageway.

Processor 20 may analyze the magnitude of the reflected power or voltage from each electrode for changes in reflected power or voltage, which would indicate changes in tissue state as the energy emitting portion 48 is moved along the passageway. For example, as previously noted it is understood that cancerous tissue possesses a lower characteristic impedance compared to that of healthy tissue of the same type. Thus, where the transmission line 58 is tuned to have an impedance matching that of healthy tissue at diagnosis site 60, movement of an electrode 56 from healthy tissue to cancerous tissue can cause an increase in the reflected power or voltage. In other embodiments, the transition from healthy tissue to diseased tissue may be reflected by a change in impedance.

In various embodiments, processor 20 may be configured to monitor the magnitude of the reflected power or voltage signal as the energy emitting portion 48 is moved along the passageway. Any method of signal processing, including measuring the derivative of the reflected power signal as a function of longitudinal movement (or time, assuming constant longitudinal movement) can be used to detect a change in slope which reflects a tissue change.

In some embodiments, the magnitude of the reflected power and/or voltage signal can be displayed to the operator, for example, via a screen.

In some embodiments, processor 20 may be configured to compare the magnitude of the reflected power or voltage signal to a pre-set threshold to determine if the magnitude of the reflected power signal reaches or passes the pre-set threshold value. In those embodiments, operator may be notified when the magnitude of the reflected power or voltage exceeds the threshold, which may indicate the presence of diseased tissue such as cancerous tissue.

In some embodiments, processor 20 may be configured to compare changes in the magnitude of the reflected power or voltage signal (e.g., a percent change) to a pre-set threshold value. In those embodiments, operator may be notified when the change in magnitude of the reflected power or voltage exceeds the threshold, which may indicate a change in tissue state, for example, a change from healthy tissue to diseased tissue such as cancerous tissue.

In some embodiments, the energy emitting portion 48 comprises a number of electrodes 56 and remains stationary within the passageway as the reflected power associated with the individual electrodes 56 is measured, whereby allowing the passageway to be mapped without moving the energy emitting portion 48. Analogous to the embodiments above, the magnitude of the reflected power may change (i.e., increase or decrease) change from one electrode 56 to another, indicating a change in tissue impedance and thus a change in tissue state.

As in the embodiments above, bi-directional coupler 62 may be configured to sample the signal passing therethrough and output a first signal 64 indicative of forward power and a second signal 66 indicative of reflective power to first monitoring device 68 and second monitoring device 70, respectively. For example, second monitoring device 70 may monitor the second signal 66 corresponding to the reflected power at each electrode position. In particular, second monitoring device 70 may monitor second signal 66 to measure the magnitude of the reflected power or voltage. Second monitoring device 70 may then transmit the measured value to processor 20.

Processor 20 may analyze the magnitude of the reflected power or voltage from each electrode for changes in reflected power or voltage between electrodes, which could indicate changes in the state of the tissue adjacent to the electrodes. For example, as noted above, it is understood that diseased tissue such as cancerous tissue generally possesses a lower characteristic impedance compared to that of healthy tissue of the same type. Thus, where the transmission line 58 is tuned to have an impedance similar to the healthy tissue at diagnosis site 60, the presence of cancerous tissue would be detected by an increased value for the reflected power or voltage.

In some embodiments, the magnitude of the reflected power or voltage signal can be conveyed to the operator, for example, via a screen.

In some embodiments, processor 20 may be configured to compare the magnitude of the reflected power or voltage signal from each electrode to a preset threshold to determine of the magnitude of the reflected power signal is greater than or equal to the pre-set threshold value, which may indicate the presence of diseased tissue such as cancerous tissue in some cases. In those embodiments, the electrodes for which the magnitude of the reflected power signal is greater than or equal to the pre-set threshold value may be displayed to the operator, for example, via a screen.

In some embodiments, processor 20 may be configured to compare the magnitude of the reflected power or voltage signal to some baseline value for the reflected power or voltage signal (e.g., the average reflected power and/or average reflected voltage). In those embodiments, each electrode for which the magnitude of the reflected power or voltage signal is greater than baseline value by a predetermined amount (e.g., by a predetermined percentage) may be displayed to the operator, for example, via a screen.

In certain embodiments, reflected low-power RF energy may be analyzed to determine if the at least one electrode 56 is in contact with the tissue at diagnosis site 60, as described in detail in U.S. Patent Pub. No. 2013/0324995.

In certain embodiments, high-power RF energy may also be delivered through the at least one electrode 56 in contact with tissue at diagnosis site 60 in order to raise a temperature of the tissue to a threshold temperature that ablates or otherwise alters the target tissue. Such power may be applied based on the results of the tissue analysis at low-power RF energy.

What is claimed is:

1. A method for diagnosing disease-state tissue of a passageway in a body comprising:
    positioning a medical device in the passageway adjacent the tissue, the medical device comprising an energy emitting portion that comprises a plurality of electrodes positioned both around a circumference of the energy emitting portion and along a length of the energy emitting portion;
    supplying an amount of low-power RF energy from an energy source to the energy emitting portion to diagnose the tissue, a first portion of the amount of low-power RF energy being transmitted through the energy emitting portion to the tissue and a second portion of the amount of low-power RF energy being reflected back towards the medical device;
    monitoring a signal corresponding to the second portion for each of the plurality of electrodes, wherein the second portion associated with individual electrodes is measured; and
    analyzing the signal to determine a presence or absence of said disease-state tissue.

2. The method of claim 1, wherein the power of the second portion, the voltage of the second portion, or both the power and voltage of the second portion are measured.

3. The method of claim 1, further comprising monitoring a signal corresponding to the first portion.

4. The method of claim 1, further comprising expanding the energy emitting portion from a collapsed configuration to an expanded configuration such that the plurality of electrodes contact tissue.

5. The method of claim 1, further comprising advancing the energy emitting portion along the passageway.

6. The method of claim 5, wherein the signal is monitored continuously as the energy emitting portion is advanced, or wherein the signal is monitored at a plurality of discrete positions.

7. The method of claim 1, wherein the signal monitored for each of the plurality of electrodes is compared to a threshold value.

8. The method of claim 1, wherein the signal monitored for each of the plurality of electrodes is compared to a signal monitored for another of the plurality of electrodes or to a baseline signal based on a collection of electrodes.

9. The method of claim 1, wherein the passageway is a mucosa-lined passageway and wherein submucosal tissue is diagnosed.

10. The method of claim 9, wherein the plurality of electrodes are operated as bipolar pairs.

11. The method of claim 10, further comprising moving the energy emitting portion longitudinally within the passageway, wherein the signal corresponding to the second portion is monitored continuously during movement and wherein the passageway is mapped.

12. The method of claim 9, wherein the disease-state tissue is cancerous tissue.

13. A system for diagnosing disease-state tissue of a passageway within a body, the system comprising:
an energy source;
a medical device configured to deliver energy to a diagnosis site in the passageway, the medical device comprising an elongate member having a proximal end and a distal end, and an energy emitting portion comprising a plurality of electrodes adjacent the distal end, the plurality of electrodes being positioned both around a circumference of the energy emitting portion and along a length of the energy emitting portion and being operable as bipolar pairs, the medical device being configured to receive an amount of low-power RF energy from the energy source, a first portion of the amount of low-power RF energy being transmitted through the energy emitting portion to the tissue and a second portion of the amount of low-power RF energy being reflected back towards the proximal end of the elongate member;
one or more components configured to detect at least a signal corresponding to the second portion of the amount of energy; and
a controller configured to analyze the signal to determine a presence or absence of said disease-state tissue.

14. The system of claim 13, wherein the one or mom components comprise a directional coupler that is configured to detect a signal corresponding to the first portion of the amount of low-power RF energy and the signal corresponding to the second portion of the amount of low-power RF energy.

15. The system of claim 13, wherein the energy source is a low-power RF generator.

16. The system of claim 13, wherein the controller is configured to analyze the signal to map the passageway.

17. A system for diagnosing disease-state tissue of a passageway within a body, the system comprising:
an energy source;
a medical device configured to deliver energy to a diagnosis site in the passageway, the medical device comprising an elongate member having a proximal end and a distal end, and an energy emitting portion adjacent the distal end comprising a plurality of electrodes disposed upon an expandable member, the plurality of electrodes being positioned both around a circumference of the expandable member and along a length of the expandable member and being operable as bipolar pairs, the medical device being configured to receive an amount of low-power RF energy from the energy source and to transmit a first portion of the amount of low-power RF energy through the energy emitting portion to the tissue;
one or more components configured to detect at least a signal corresponding to a second portion of the amount of low-power energy that is reflected back towards the proximal end of the elongate member; and
a controller configured to analyze the signal to determine a presence or absence of said disease-state tissue.

18. The system of claim 17, wherein the plurality of electrodes are elongated electrodes that extend lengthwise along the expandable member.

19. The system of claim 17, wherein the expandable member is an expandable frame or an expandable balloon.

20. The system of claim 17, wherein the controller is configured to analyze the signal to map the passageway.

* * * * *